United States Patent
Kadam et al.

(10) Patent No.: US 11,208,375 B2
(45) Date of Patent: Dec. 28, 2021

(54) PROCESS FOR MAKING SOLID METHYLGLYCINE DIACETATE (MGDA) ALKALI METAL SALT, AND SOLID PARTICLES

(71) Applicant: BASF SE, Ludwigshafen am Rhein (DE)

(72) Inventors: Somnath Shivaji Kadam, Ludwigshafen (DE); Frank Jaekel, Ludwigshafen (DE); Feely Ruether, Ludwigshafen (DE); Lothar Karrer, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 70 days.

(21) Appl. No.: 16/484,016

(22) PCT Filed: Feb. 20, 2018

(86) PCT No.: PCT/EP2018/054185
§ 371 (c)(1),
(2) Date: Aug. 6, 2019

(87) PCT Pub. No.: WO2018/153876
PCT Pub. Date: Aug. 30, 2018

(65) Prior Publication Data
US 2020/0095189 A1     Mar. 26, 2020

(30) Foreign Application Priority Data
Feb. 24, 2017  (EP) .................................. 17157850

(51) Int. Cl.
| C11D 7/32   | (2006.01) |
| C11D 7/02   | (2006.01) |
| C07C 227/42 | (2006.01) |
| B01D 9/00   | (2006.01) |
| C07C 229/16 | (2006.01) |
| C11D 3/33   | (2006.01) |
| C11D 3/39   | (2006.01) |

(52) U.S. Cl.
CPC .......... *C07C 227/42* (2013.01); *B01D 9/0036* (2013.01); *C07C 229/16* (2013.01); *C11D 3/33* (2013.01); *C11D 3/39* (2013.01); *C11D 7/02* (2013.01); *C11D 7/3245* (2013.01); *B01D 2009/0086* (2013.01)

(58) Field of Classification Search
CPC ............ C11D 3/33; C11D 7/3245; C11D 7/02
USPC ......................................... 510/477, 488, 499
See application file for complete search history.

(56) References Cited

U.S. PATENT DOCUMENTS

| 5,981,798 A      | 11/1999 | Schoenherr et al. |              |
| 8,048,838 B2 *   | 11/2011 | Witteler          | C11D 3/3776  |
|                  |         |                   | 510/224      |
| 9,802,884 B2 *   | 10/2017 | Garcia            | C11D 3/33    |
| 2011/0150787 A1* | 6/2011  | Gonzales          | A61Q 11/00   |
|                  |         |                   | 424/49       |
| 2012/0046491 A1  | 2/2012  | Mrzena et al.     |              |
| 2012/0149936 A1  | 6/2012  | Baranyai          |              |
| 2012/0283473 A1  | 11/2012 | Oftring et al.    |              |
| 2014/0155646 A1  | 6/2014  | Mrzena et al.     |              |
| 2015/0007400 A1* | 1/2015  | Gonzales          | A61K 8/8117  |
|                  |         |                   | 15/104.93    |
| 2015/0105831 A1* | 4/2015  | Yim               | A61B 17/7091 |
|                  |         |                   | 606/86 A     |
| 2016/0221930 A1  | 8/2016  | Baranyai          |              |
| 2017/0158613 A1  | 6/2017  | Schomaker et al.  |              |

FOREIGN PATENT DOCUMENTS

| DE | 198 19 187 A1     | 11/1999 |           |
| EP | 0 845 456 A2      | 6/1998  |           |
| EP | 0 845 846 A1      | 6/1998  |           |
| EP | 0 851 023 A2      | 7/1998  |           |
| EP | 2 470 496 A1      | 7/2012  |           |
| WO | WO 2010/133618 A1 | 11/2010 |           |
| WO | WO 2014/086662 A1 | 6/2014  |           |
| WO | WO-2015036324 A1* | 3/2015  | C07C 253/00 |
| WO | WO 2015/173157 A2 | 11/2015 |           |

OTHER PUBLICATIONS

Extended European Search Report dated Aug. 17, 2017, in Patent Application No. 17157850.3, 4 pages.
International Search Report dated Apr. 25, 2018 in PCT/EP2018/054185 filed Feb. 20, 2018.
U.S. Appl. No. 16/485,188, filed Aug. 12, 2019, Stephan Hueffer.

* cited by examiner

*Primary Examiner* — Gregory R Delcotto
(74) *Attorney, Agent, or Firm* — Arent Fox LLP

(57) ABSTRACT

Process for making solid methylglycine diacetate (MGDA) alkali metal salt (a), said process comprising the steps of (A) providing a 35 to 60% by weight aqueous solution of said MGDA salt having a temperature in the range of from 50 to 90° C., (B) adding 0.01 to 2% by weight of a particulate solid with a pore volume in the range of from 0.25 to 0.75 cm$^3$/g, determined by nitrogen adsorption in accordance with 66134:1998-02 (b), the percentage referring to the content of (a), (C) crystallizing (a), (D) removing said crystalline (a) from the mother liquor.

15 Claims, No Drawings

PROCESS FOR MAKING SOLID METHYLGLYCINE DIACETATE (MGDA) ALKALI METAL SALT, AND SOLID PARTICLES

The present invention relates to a process for making solid methylglycine diacetate (MGDA) alkali metal salt (a), said process comprising the steps of
(A) providing a 35 to 60% by weight aqueous solution of said MGDA salt having a temperature in the range of from 50 to 90° C.,
(B) adding 0.01 to 2% by weight of a particulate solid with a pore volume in the range of from 0.25 to 0.75 cm$^3$/g, determined by nitrogen adsorption in accordance with 66134:1998-02 (b), the percentage referring to the content of (a),
(C) crystallizing (a),
(D) removing said crystalline (a) from the mother liquor.
In addition, the present invention relates to solid particles comprising MGDA.

Chelating agents such as methyl glycine diacetic acid (MGDA) and their respective alkali metal salts are useful sequestrants for alkaline earth metal ions such as $Ca^{2+}$ and $Mg^{2+}$. For that reason, they are recommended and used for various purposes such as laundry detergents and for automatic dishwashing (ADW) formulations, in particular for so-called phosphate-free laundry detergents and phosphate-free ADW formulations. For shipping such chelating agents, in most cases either solids such as powders or granules are being applied or aqueous solutions.

Depending on the type of product—liquid home care and fabric care products versus solid home care and fabric care products—and the manufacturing process of solid home care and fabric care products care product manufacturers may either prefer to handle solutions of aminocarboxylates or solid aminocarboxylates, for example joint spray drying or solid mixing. Powders and granules of aminocarboxylates may be shipped economically due to their high active ingredient content that goes along with low water content. Therefore, convenient processes for providing granules are still of great commercial interest.

However, granules and powders of MGDA and its respective alkali metal salts may be hygroscopic depending on the way they were obtained. Such hygroscopicity is undesired for various reasons. In powdery care formulations, the water may lead to lump formation that prevent the care formulation from flowing freely where desired. In addition, the water may create a medium wherein components of a formulation may react with and deactivate each other, for example bleaching agents and enzymes. Strongly hygroscopic mixtures may additionally show a tendency to yellowing when stored with percarbonate. Even in cases where the yellow colour does not prove a deterioration in quality consumers tend to avoid yellowing formulations.

In EP 0 845 846 A, a process to make crystalline salts of MGDA is disclosed. A water-containing super-cooled melt of MGDA is seeded with MGDA powder. The process has its shortcomings, though, because it is tedious to remove the crystals from the crystallization vessel.

It was the objective of the present invention to provide a process that leads to MGDA or its salts in solid form with low hygroscopicity. It was furthermore an objective to provide solids of MGDA or its salts with low hygroscopicity.

Accordingly, the process defined at the outset has been found, hereinafter also referred to as inventive process or process according to the present invention.

The inventive process is a process for making solid MGDA or its respective alkali metal salts, for example in form of a powder or of a granule. In the context of the present invention, the term "powder" refers to particulate materials that are solids at ambient temperature and that preferably have an average particle diameter in the range of from 100 nm to less than 0.1 mm, preferably 30 μm up to 75 μm. The average particle diameter of powders can be determined, e.g., by LASER diffraction methods, for example with a Malvern apparatus, and refers to the volume average.

The term "granule" in the context of the present invention refers to particulate materials that are solids at ambient temperature and that preferably have an average particle diameter (D50) in the range of from 0.1 mm to 2 mm, preferably 0.4 mm to 1.25 mm, even more preferably 400 μm to 1 mm. The average particle diameter of granules can be determined, e.g., by optical or preferably by sieving methods. Sieves employed may have a mesh in the range of from 60 to 3,000 μm.

The inventive process comprises of several steps, hereinafter in brief also referred to as step (A), step (B), step (C) and step (D) or (A), (B), (C) or (D), respectively. Step (A), step (B), step (C) and step (D) will be outlined in more detail below.

As mentioned above, in step (A) an aqueous solution is provided. Aqueous solutions are defined herein as solutions with no solid particles detectable by visual inspection. Aqueous solutions may contain minor amounts of organic solvent that is or are miscible with water, for example ethanol, 1,2-propylenglycol, ethylene glycol, for example in a volume ration water:organic solvent 5:1 to 100:1. Preferably, however, aqueous solutions provided in step (A) do not contain detectable amounts of organic solvent.

Alkali metal salts of MGDA, hereinafter also referred to as component (a) or briefly (a), refers to methylglycine, partially or fully neutralized with alkali metal. Preferred examples of alkali metals are sodium and potassium and combinations of sodium and potassium.

In a preferred embodiment of the present invention, alkali metals of MGDA are selected from compounds according to general formula (I)

$$[CH_3—CH(COO)—N(CH_2—COO)_2]M_{3-x}H_x \qquad (I)$$

wherein
M is selected from alkali metal cations, same or different, for example cations of lithium, sodium, potassium, rubidium, cesium, and combinations of at least two of the foregoing. Preferred examples of alkali metal cations are sodium and potassium and combinations of sodium and potassium.

x in formula (I) is in the range of from zero to 1.0, preferred are zero to 0.5. In a particularly preferred embodiment, x is zero.

In one embodiment of the present invention, alkali metal salts of MGDA are selected from lithium salts, potassium salts and preferably sodium salts of MGDA. MGDA can be partially or preferably fully neutralized with the respective alkali. In a preferred embodiment, an average of from 2.7 to three COOH groups of MGDA is neutralized with alkali metal, preferably with sodium. In a particularly preferred embodiment, component (a) is the trisodium salt of MGDA.

MGDA and its respective alkali metal salts are selected from the racemic mixtures, the D-isomers and the L-isomers, and from mixtures of the D- and L-isomers other than the racemic mixtures. Preferably, component (a) is selected from the racemic mixture and from mixtures containing in the range of from 55 to 95 mole-% of the L-isomer, the balance being D-isomer. Particularly preferred are mixtures containing in the range of from 60 to 80 mole-% of the L-isomer, the balance being D-isomer. Other particularly preferred embodiments are racemic mixtures.

In any way, minor amounts of component (a) may bear a cation other than alkali metal. It is thus possible that minor amounts, such as 0.01 to 5 mol-% of total (a), bear alkali earth metal cations such as $Mg^{2+}$ or $Ca^{2+}$, or an $Fe^{2+}$ or $Fe^{3+}$ cation, or ammonium ($NH_4^+$).

In one embodiment of the present invention, component (a) may contain one or more impurities that may result from the synthesis of the MGDA. Examples of such impurities may be selected from propionic acid, lactic acid, alanine, nitrilotriacetic acid ("NTA") or the like and their respective alkali metal salts. In the case of IDS, such impurities may be selected from maleic acid, monoamides of maleic/fumaric acid, and racemic asparagine. Such impurities are usually present in minor amounts. "Minor amounts" in this context refer to a total of 0.1 to 5% by weight, referring to component (a), preferably up to 2.5% by weight. In the context of the present invention, such minor amounts are neglected when determining the concentration of the aqueous solution provided in step (A).

The aqueous solution provided in step (A) has a concentration of component (a) In the range of from 35 to 60% by weight, preferably 40 to 50% by weight and even more preferably 45 to 50% by weight.

The aqueous solution provided in step (A) has a temperature in the range of from 50 to 90° C., preferably 60 to 80° C.

In one embodiment of the present invention, such aqueous solution according to step (A) has a pH value in the range of from 8 to 14, preferably from 9 to 13.5 and even more preferably at least 9.5. The pH value is determined at ambient temperature.

Solutions according to step (A) may be obtained by various methods. It is possible, e.g., to heat a given aqueous solution of component (a) to 50 to 90° C., or to dissolve component (a) in water under heating and, if applicable, removal of some of the water, for example by evaporation. In an alternative embodiment, it is possible to start the inventive process with a solution of component (a) that is stemming directly from the synthesis, in particular the saponification step, and to incompletely cool down such solution.

In step (B), an amount of 0.01 to 2% by weight of a particulate solid, said particulate solid also being referred to as solid (b), with a pore volume in the range of from 0.25 to 0.75 $cm^3/g$ is added to the solution provided in step (A), wherein the pore volume is determined by nitrogen adsorption in accordance with DIN 66134:1998-02 (b), the percentage referring to the content of (a). Preferably, the porosity is in the range of from 40 to 85%. The method is also known as Barrett, Joyner and Halenda method or BJH method.

Preferred amount of solid (b) is 0.1 to 1.5% by weight, and even more preferred are 0.5 to 1.0% by weight.

In a preferred embodiment of the present invention, solid (b) has a specific surface (BET) in the range of from 150 to 500 $m^2/g$, preferably 300 to 400 $m^2/g$, preferably determined according to DIN ISO 9277:2003-05.

Solid (b) is a particulate solid. In one embodiment of the present invention, solid (b) has an average particle diameter in the range of from 10 to 1000 μm, preferably 350 to 750 μm as determined by sieving.

Examples of solids (b) are molecular sieves, silicon, and especially alumina, preferably in the ground state.

Preferred examples of molecular sieves are zeolites, thus alumosilicates with a molar silica/alumina ratio of about 1:1, furthermore silica and mesoporous silica, and clays such as montmorillonites.

A suitable form of silicon is powdery silicon for wafer manufacture or from milled wafers or ground wafers.

Alumina is particularly preferred, for example $\alpha$-$Al_2O_3$ (alpha-alumina) or $\gamma$-$Al_2O_3$ (gamma-alumina) or amorphous alumina. Examples of particularly preferred alumina are alumina with a packed bulk density of 769 $kg/m^3$, a total pore volume of 0.4 to 0.5 $cm^3/g$, and a specific surface area (BET) in the range of from 320 to 360 $m^2/g$ and after grinding an average particle diameter in the range from 350-750 μm.

Step (B) may be carried out by adding several aliquots of solid (b) or by adding all the solid (b) in one portion, the latter being preferred.

Step (B) may be performed without agitation or preferably under agitation, for example shaking or stirring, stirring being more preferred.

Step (B) leads to formation of crystals.

In step (C), (a) is crystallized. Step (C) may be performed under agitation, for example shaking or stirring, or without stirring.

During step (C), crystallization may be enhanced by cooling of the solution of (a), or by allowing it to cool. By such cooling, the temperature may be decreased by 20 to 80° C. By cooling—or allowing to cool—the solution of (a), a slurry is obtained. It is noted that a solution provided in step (A) that has a temperature of about 90° C. may be cooled by up to 80° C. The final temperature should be at least zero ° C., preferably at least 10° C. and even more preferably at least 20° C.

During step (C), crystals of (a) are not only formed directly by seeding and thus with at least one particle of (b) inside but also in the neighborhood of particles of (b). Without wishing to be bound by any theory we feel that ten by 20 times as many particles form compared to solid (b) added in step (B).

Crystals of (a) are hereinafter also referred to as crystalline (a).

In step (D), said crystalline (a) is removed from the mother liquor. Such removal may be performed by filtration, for example with a belt filter or a strainer. The filter may have a pore diameter in the range of from 7 to 30 μm. Operations such as one or more washing steps and drying, for example vacuum drying, may be performed after filtration.

The inventive process also furnishes a mother liquor that may be "recycled", for example by adding solid alkali metal salt of MGDA and again performing the inventive process.

In a special embodiment, some crystalline (a) obtained by the inventive process may be recycled using them as seed instead of solid (b), optionally after milling them down to an average particle diameter of 250 to 750 μm.

The yield of crystalline (a) may be in the range of from 10 to 95%, preferably 60 to 95%, referring to dissolved (a).

Crystalline salts of MGDA are obtained by the inventive process. They exhibit a remarkably low hygroscopicity and a particularly good stability towards percarbonates such as sodium percarbonate.

Another aspect of the present invention is related to solid particles of methylglycine diacetate (MGDA) alkali metal salt (a)—hereinafter also referred to as inventive solid particles—containing (a1) in the range of from 1 to 10% by weight monoclinic alkali metal salt of MGDA, preferably 3 to 7% by weight, (a2) in the range of from 90 to 99% by weight orthorhombic alkali metal salt of MGDA, preferably 93 to 97% by weight, percentages referring to the entire content of the respective alkali metal salt of MGDA (a).

The crystal forms are determined by powder X-ray diffraction.

In one embodiment of the present invention, (a) is selected from compounds according to general formula (I)

[CH$_3$—CH(COO)—N(CH$_2$—COO)$_2$]M$_{3-x}$H$_x$ (I)

wherein

M is selected from alkali metal cations, same or different, for example cations of lithium, sodium, potassium, rubidium, cesium, and combinations of at least two of the foregoing. Preferred examples of alkali metal cations are sodium and potassium and combinations of sodium and potassium.

x in formula (I) is in the range of from zero to 1.0, preferred are zero to 0.5. In a particularly preferred embodiment, x is zero.

Even more preferred is the trisodium salt—

In one embodiment of the present invention, inventive solid particles contain the racemic mixture of a component (a). In other embodiments, component (a) in inventive solid particles is elected from the D-isomer and the L-isomers, and from mixtures of the D- and L-isomers other than the racemic mixtures. Preferably, component (a) in inventive solid particles is selected from the racemic mixture and from mixtures containing in the range of from 55 to 95 mole-% of the L-isomer, the balance being D-isomer. Particularly preferred are mixtures containing in the range of from 60 to 80 mole-% of the L-isomer, the balance being D-isomer. Other particularly preferred embodiments are racemic mixtures.

In one embodiment of the present invention, in the range of from 0.1 to 30% of the particles contain residual solid (b). Solid (b) has been defined above.

In one embodiment of the present invention solid (b) is selected from molecular sieves, alumina and silicon, in particular alumina.

In one embodiment of the present invention, inventive solid particles have an average particle diameter in the range of from 100 nm to 500 μm, preferably 10 to 100 μm.

In one embodiment of the present invention, inventive solid particles have a residual moisture content in the range of from 0.5 to 20%, preferably 9 to 15% by weight. The residual moisture content may be determined, e.g., by Karl-Fischer titration.

Another aspect of the present invention is directed towards the use of inventive solid particles according in or for making a cleaning agent that contains a peroxide or a percarbonate.

Another aspect of the present invention relates to the use of inventive solid particles, and another aspect of the present invention relates to methods of use of inventive solid particles. The preferred use of inventive solid particles is for the manufacture of solid cleaning agents such as solid laundry detergent compositions and of solid detergent compositions for hard surface cleaning. Solid laundry detergent compositions and solid detergent compositions for hard surface cleaning may contain some residual moisture, for example 0.1 to 10% by weight, but are otherwise solid mixtures. The residual moisture content may be determined, e.g., under vacuum at 80° C. Another aspect of the present invention relates to solid laundry detergent compositions and to solid detergent compositions for hard surface cleaning.

In the context of the present invention, the term "detergent composition for cleaners" includes cleaners for home care and for industrial or institutional applications. The term "detergent composition for hard surface cleaners" includes compositions for dishwashing, especially hand dishwash and automatic dishwashing and ware-washing, and compositions for other hard surface cleaning such as, but not limited to compositions for bathroom cleaning, kitchen cleaning, floor cleaning, descaling of pipes, window cleaning, car cleaning including truck cleaning, furthermore, open plant cleaning, cleaning-in-place, metal cleaning, disinfectant cleaning, farm cleaning, high pressure cleaning, but not laundry detergent compositions.

In the context of the present invention and unless expressly stated otherwise, percentages in the context of ingredients of laundry detergent compositions are percentages by weight and refer to the total solids content of the respective laundry detergent composition. In the context of the present invention and unless expressly stated otherwise, percentages in the context of ingredients of detergent composition for hard surface cleaning are percentages by weight and refer to the total solids content of the detergent composition for hard surface cleaner.

In one embodiment of the present invention, solid laundry detergent compositions according to the present invention may contain in the range of from 1 to 30% by weight of inventive solid particles, respectively. Percentages refer to the total solids content of the respective laundry detergent composition.

In one embodiment of the present invention, inventive solid detergent compositions for hard surface cleaning may contain in the range of from 1 to 50% by weight of inventive solid particles, respectively, preferably 5 to 40% by weight and even more preferably 10 to 25% by weight. Percentages refer to the total solids content of the respective detergent composition for hard surface cleaning.

Particularly advantageous inventive solid detergent compositions for hard surface cleaning and inventive solid laundry detergent compositions, especially for home care, may contain one or more complexing agent other than inventive solid particles. Inventive solid detergent compositions for hard surface cleaning and inventive solid laundry detergent compositions may contain one or more complexing agent (in the context of the present invention also referred to as sequestrant) other than inventive solid particles. Examples are citrate, phosphonic acid derivatives, for example the disodium salt of hydroxyethane-1,1-diphosphonic acid ("HEDP"), and polymers with complexing groups like, for example, polyethyleneimine in which 20 to 90 mole-% of the N-atoms bear at least one CH$_2$COO$^-$ group, and their respective alkali metal salts, especially their sodium salts, for example GLDA-Na$_4$, IDS-Na$_4$, and trisodium citrate, and phosphates such as STPP (sodium tripolyphosphate). Due to the fact that phosphates raise environmental concerns, it is preferred that advantageous detergent compositions for cleaners and advantageous laundry detergent compositions are free from phosphate. "Free from phosphate" should be understood in the context of the present invention, as meaning that the content of phosphate and polyphosphate is in sum in the range from 10 ppm to 0.2% by weight, determined by gravimetric methods.

Preferred inventive solid detergent compositions for hard surface cleaning and preferred inventive solid laundry detergent compositions may contain one or more surfactant, preferably one or more non-ionic surfactant.

Preferred non-ionic surfactants are alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (III)

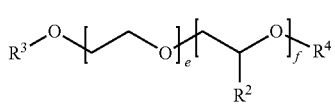
(III)

in which the variables are defined as follows:
$R^2$ is identical or different and selected from hydrogen and linear $C_1$-$C_{10}$-alkyl, preferably in each case identical and ethyl and particularly preferably hydrogen or methyl,
$R^3$ is selected from $C_8$-$C_{22}$-alkyl, branched or linear, for example n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
$R^4$ is selected from $C_1$-$C_{10}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or isodecyl,
m and n are in the range from zero to 300, where the sum of n and m is at least one, preferably in the range of from 3 to 50. Preferably, m is in the range from 1 to 100 and n is in the range from 0 to 30.

In one embodiment, compounds of the general formula (III) may be block copolymers or random copolymers, preference being given to block copolymers.

Other preferred examples of alkoxylated alcohols are, for example, compounds of the general formula (IV)

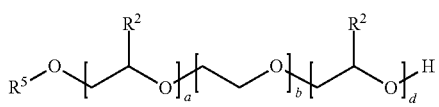
(IV)

in which the variables are defined as follows:
$R^2$ is identical or different and selected from hydrogen and linear $C_1$-$C_{10}$-alkyl, preferably identical in each case and ethyl and particularly preferably hydrogen or methyl,
$R^5$ is selected from $C_6$-$C_{20}$-alkyl, branched or linear, in particular n-$C_8H_{17}$, n-$C_{10}H_{21}$, n-$C_{12}H_{25}$, n-$C_{13}H_{27}$, n-$C_{15}H_{31}$, n-$C_{14}H_{29}$, n-$C_{16}H_{33}$, n-$C_{18}H_{37}$,
a is a number in the range from zero to 10, preferably from 1 to 6,
b is a number in the range from 1 to 80, preferably from 4 to 20,
d is a number in the range from zero to 50, preferably 4 to 25.

The sum a+b+d is preferably in the range of from 5 to 100, even more preferably in the range of from 9 to 50.

Preferred examples for hydroxyalkyl mixed ethers are compounds of the general formula (V)

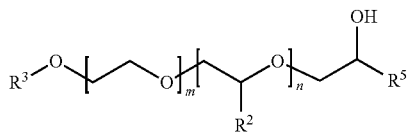
(V)

in which the variables are defined as follows:
$R^2$ is identical or different and selected from hydrogen and linear $C_1$-$C_{10}$-alkyl, preferably in each case identical and ethyl and particularly preferably hydrogen or methyl,
$R^3$ is selected from $C_8$-$C_{22}$-alkyl, branched or linear, for example iso-$C_{11}H_{23}$, iso-$C_{13}H_{27}$, n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
$R^5$ is selected from $C_6$-$C_{20}$-alkyl, for example n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The variables m and n are in the range from zero to 300, where the sum of n and m is at least one, preferably in the range of from 5 to 50. Preferably, m is in the range from 1 to 100 and n is in the range from 0 to 30.

Compounds of the general formula (IV) and (V) may be block copolymers or random copolymers, preference being given to block copolymers.

Further suitable nonionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{16}$-alkyl polyglucosides and branched $C_8$-$C_{14}$-alkyl polyglycosides such as compounds of general average formula (VI) are likewise suitable.

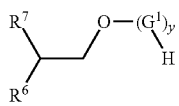
(VI)

wherein:
$R^6$ is $C_1$-$C_4$-alkyl, in particular ethyl, n-propyl or isopropyl,
$R^7$ is —$(CH_2)_2$—$R^6$,
$G^1$ is selected from monosaccharides with 4 to 6 carbon atoms, especially from glucose and xylose,
y in the range of from 1.1 to 4, y being an average number,
Further examples of non-ionic surfactants are compounds of general formula (VII) and (VIII)

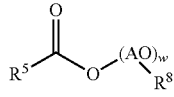
(VII)

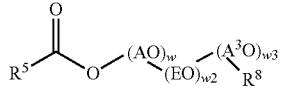
(VIII)

AO is selected from ethylene oxide, propylene oxide and butylene oxide,
EO is ethylene oxide, $CH_2CH_2$—O,
$R^8$ selected from $C_8$-$C_{18}$-alkyl, branched or linear, and $R^5$ is defined as above.

$A^3O$ is selected from propylene oxide and butylene oxide,
w is a number in the range of from 15 to 70, preferably 30 to 50,
w1 and w3 are numbers in the range of from 1 to 5, and
w2 is a number in the range of from 13 to 35.

An overview of suitable further nonionic surfactants can be found in EP-A 0 851 023 and in DE-A 198 19 187.

Mixtures of two or more different nonionic surfactants selected from the foregoing may also be present.

Other surfactants that may be present are selected from amphoteric (zwitterionic) surfactants and anionic surfactants and mixtures thereof.

Examples of amphoteric surfactants are those that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteric surfactants is cocamidopropyl betaine (lauramidopropyl betaine).

Examples of amine oxide surfactants are compounds of the general formula (IX)

$$R^9R^{10}R^{11}N \rightarrow O \quad (IX)$$

wherein $R^9$, $R^{10}$, and $R^{11}$ are selected independently from each other from aliphatic, cycloaliphatic or $C_2$-$C_4$-alkylene $C_{10}$-$C_{20}$-alkylamido moieties. Preferably, $R^9$ is selected from $C_8$-$C_{20}$alkyl or $C_2$-$C_4$-alkylene $C_{10}$-$C_{20}$-alkylamido and $R^{10}$ and $R^{11}$ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

Examples of suitable anionic surfactants are alkali metal and ammonium salts of $C_8$-$C_{18}$-alkyl sulfates, of $C_8$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{18}$-alkylsulfonic acids and of $C_{10}$-$C_{18}$-alkylarylsulfonic acids. Preference is given to the alkali metal salts of the aforementioned compounds, particularly preferably the sodium salts.

Further examples for suitable anionic surfactants are soaps, for example the sodium or potassium salts of stearic acid, oleic acid, palmitic acid, ether carboxylates, and alkylether phosphates.

Preferably, inventive laundry detergent compositions contain at least one anionic surfactant.

In one embodiment of the present invention, inventive solid laundry detergent compositions may contain 0.1 to 60% by weight of at least one surfactant, selected from anionic surfactants, amphoteric surfactants and amine oxide surfactants.

In one embodiment of the present invention, inventive solid detergent compositions for cleaners may contain 0.1 to 60% by weight of at least one surfactant, selected from anionic surfactants, amphoteric surfactants and amine oxide surfactants.

In a preferred embodiment, inventive solid detergent compositions for cleaners and especially those for automatic dishwashing do not contain any anionic surfactant.

Inventive solid detergent compositions for hard surface cleaning and inventive solid laundry detergent compositions may contain at least one bleaching agent, also referred to as bleach. Bleaching agents may be selected from chlorine bleach and peroxide bleach, and peroxide bleach may be selected from inorganic peroxide bleach and organic peroxide bleach. Preferred are inorganic peroxide bleaches, selected from alkali metal percarbonate, alkali metal perborate and alkali metal persulfate.

Examples of organic peroxide bleaches are organic percarboxylic acids, especially organic percarboxylic acids.

In inventive solid detergent compositions for hard surface cleaning and in inventive solid laundry detergent compositions, alkali metal percarbonates, especially sodium percarbonates, are preferably used in coated form. Such coatings may be of organic or inorganic nature. Examples are glycerol, sodium sulfate, silicate, sodium carbonate, and combinations of at least two of the foregoing, for example combinations of sodium carbonate and sodium sulfate.

Suitable chlorine-containing bleaches are, for example, 1,3-dichloro-5,5-dimethylhydantoin, N-chlorosulfamide, chloramine T, chloramine B, sodium hypochlorite, calcium hypochlorite, magnesium hypochlorite, potassium hypochlorite, potassium dichloroisocyanurate and sodium dichloroisocyanurate.

Inventive solid detergent compositions for hard surface cleaning and inventive solid laundry detergent compositions may comprise, for example, in the range from 3 to 10% by weight of chlorine-containing bleach.

Inventive solid detergent compositions for hard surface cleaning and inventive solid laundry detergent compositions may comprise one or more bleach catalysts. Bleach catalysts can be selected from bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and also cobalt-, iron-, copper- and ruthenium-amine complexes can also be used as bleach catalysts.

Inventive solid detergent compositions for hard surface cleaning and inventive solid laundry detergent compositions may comprise one or more bleach activators, for example N-methylmorpholinium-acetonitrile salts ("MMA salts"), trimethylammonium acetonitrile salts, N-acylimides such as, for example, N-nonanoylsuccinimide, 1,5-diacetyl-2,2-dioxohexahydro-1,3,5-triazine ("DADHT") or nitrile quats (trimethylammonium acetonitrile salts).

Further examples of suitable bleach activators are tetraacetylethylenediamine (TAED) and tetraacetylhexylenediamine.

Inventive solid detergent compositions for hard surface cleaning and inventive solid laundry detergent compositions may comprise one or more corrosion inhibitors. In the present case, this is to be understood as including those compounds which inhibit the corrosion of metal. Examples of suitable corrosion inhibitors are triazoles, in particular benzotriazoles, bisbenzotriazoles, aminotriazoles, alkylaminotriazoles, also phenol derivatives such as, for example, hydroquinone, pyrocatechol, hydroxyhydroquinone, gallic acid, phloroglucinol or pyrogallol.

In one embodiment of the present invention, inventive solid detergent compositions for hard surface cleaning and inventive solid laundry detergent compositions comprise in total in the range from 0.1 to 1.5% by weight of corrosion inhibitor.

Inventive solid detergent compositions for hard surface cleaning and inventive solid laundry detergent compositions may comprise one or more builders, selected from organic and inorganic builders. Examples of suitable inorganic builders are sodium sulfate or sodium carbonate or silicates, in particular sodium disilicate and sodium metasilicate, zeolites, sheet silicates, in particular those of the formula $\alpha\text{-}Na_2Si_2O_5$, $\beta\text{-}Na_2Si_2O_5$, and $\delta\text{-}Na_2Si_2O_5$, also fatty acid sulfonates, $\alpha$-hydroxypropionic acid, alkali metal malonates, fatty acid sulfonates, alkyl and alkenyl disuccinates, tartaric acid diacetate, tartaric acid monoacetate, oxidized starch, and polymeric builders, for example polycarboxylates and polyaspartic acid.

Examples of organic builders are especially polymers and copolymers. In one embodiment of the present invention, organic builders are selected from polycarboxylates, for example alkali metal salts of (meth)acrylic acid homopolymers or (meth)acrylic acid copolymers.

Suitable comonomers are monoethylenically unsaturated dicarboxylic acids such as maleic acid, fumaric acid, maleic anhydride, itaconic acid and citraconic acid. A suitable polymer is in particular polyacrylic acid, which preferably has an average molecular weight $M_w$ in the range from 2000 to 40 000 g/mol, preferably 2000 to 10 000 g/mol, in particular 3000 to 8000 g/mol. Also of suitability are copolymeric polycarboxylates, in particular those of acrylic acid with methacrylic acid and of acrylic acid or methacrylic acid with maleic acid and/or fumaric acid, and in the same range of molecular weight.

It is also possible to use copolymers of at least one monomer from the group consisting of monoethylenically unsaturated $C_3$-$C_{10}$-mono- or $C_4$-$C_{10}$-dicarboxylic acids or anhydrides thereof, such as maleic acid, maleic anhydride, acrylic acid, methacrylic acid, fumaric acid, itaconic acid and citraconic acid, with at least one hydrophilic or hydrophobic monomer as listed below.

Suitable hydrophobic monomers are, for example, isobutene, diisobutene, butene, pentene, hexene and styrene, olefins with 10 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene, $C_{22}$-$\alpha$-olefin, a mixture of $C_{20}$-$C_{24}$-$\alpha$-olefins and polyisobutene having on average 12 to 100 carbon atoms per molecule.

Suitable hydrophilic monomers are monomers with sulfonate or phosphonate groups, and also nonionic monomers with hydroxyl function or alkylene oxide groups. By way of example, mention may be made of: allyl alcohol, isoprenol, methoxypolyethylene glycol (meth)acrylate, methoxypolypropylene glycol (meth)acrylate, methoxypolybutylene glycol (meth)acrylate, methoxypoly(propylene oxide-co-ethylene oxide) (meth)acrylate, ethoxypolyethylene glycol (meth)acrylate, ethoxypolypropylene glycol (meth)acrylate, ethoxypolybutylene glycol (meth)acrylate and ethoxypoly(propylene oxide-co-ethylene oxide) (meth)acrylate. Polyalkylene glycols here may comprise 3 to 50, in particular 5 to 40 and especially 10 to 30 alkylene oxide units per molecule.

Particularly preferred sulfonic-acid-group-containing monomers here are 1-acrylamido-1-propanesulfonic acid, 2-acrylamido-2-propanesulfonic acid, 2-acrylamido-2-methylpropanesulfonic acid, 2-methacrylamido-2-methylpropanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 2-sulfoethyl methacrylate, 3-sulfopropyl methacrylate, sulfomethacrylamide, sulfomethylmethacrylamide, and salts of said acids, such as sodium, potassium or ammonium salts thereof.

Particularly preferred phosphonate-group-containing monomers are vinylphosphonic acid and its salts.

A further example of builders is carboxymethyl inulin.

Moreover, amphoteric polymers can also be used as builders.

Inventive solid detergent compositions for hard surface cleaning and inventive solid laundry detergent compositions may comprise, for example, in the range from in total 10 to 70% by weight, preferably up to 50% by weight, of builder. In the context of the present invention, MGDA is not counted as builder.

In one embodiment of the present invention, inventive solid detergent compositions for hard surface cleaning and inventive solid laundry detergent compositions may comprise one or more cobuilders.

Inventive solid detergent compositions for hard surface cleaning and inventive solid laundry detergent compositions may comprise one or more antifoams, selected for example from silicone oils and paraffin oils.

In one embodiment of the present invention, inventive solid detergent compositions for hard surface cleaning and inventive solid laundry detergent compositions comprise in total in the range from 0.05 to 0.5% by weight of antifoam.

Inventive solid detergent compositions for hard surface cleaning and inventive solid laundry detergent compositions may comprise one or more enzymes. Examples of enzymes are lipases, hydrolases, amylases, proteases, cellulases, esterases, pectinases, lactases and peroxidases.

In one embodiment of the present invention, inventive solid detergent compositions for hard surface cleaning and inventive solid laundry detergent compositions may comprise, for example, up to 5% by weight of enzyme, preference being given to 0.1 to 3% by weight. Said enzyme may be stabilized, for example with the sodium salt of at least one $C_1$-$C_3$-carboxylic acid or $C_4$-$C_{10}$-dicarboxylic acid. Preferred are formates, acetates, adipates, and succinates.

In one embodiment of the present invention, inventive solid detergent compositions for hard surface cleaning and inventive solid laundry detergent compositions comprise at least one zinc salt. Zinc salts can be selected from water-soluble and water-insoluble zinc salts. In this connection, within the context of the present invention, water-insoluble is used to refer to those zinc salts which, in distilled water at 25° C., have a solubility of 0.1 g/l or less. Zinc salts which have a higher solubility in water are accordingly referred to within the context of the present invention as water-soluble zinc salts.

In one embodiment of the present invention, zinc salt is selected from zinc benzoate, zinc gluconate, zinc lactate, zinc formate, $ZnCl_2$, $ZnSO_4$, zinc acetate, zinc citrate, $Zn(NO_3)_2$, $Zn(CH_3SO_3)_2$ and zinc gallate, preferably $ZnCl_2$, $ZnSO_4$, zinc acetate, zinc citrate, $Zn(NO_3)_2$, $Zn(CH_3SO_3)_2$ and zinc gallate.

In another embodiment of the present invention, zinc salt is selected from $ZnO$, $ZnO.aq$, $Zn(OH)_2$ and $ZnCO_3$. Preference is given to $ZnO.aq$.

In one embodiment of the present invention, zinc salt is selected from zinc oxides with an average particle diameter (weight-average) in the range from 10 nm to 100 µm.

The cation in zinc salt can be present in complexed form, for example complexed with ammonia ligands or water ligands, and in particular be present in hydrated form. To simplify the notation, within the context of the present invention, ligands are generally omitted if they are water ligands.

Depending on how the pH of mixture according to the invention is adjusted, zinc salt can change. Thus, it is for example possible to use zinc acetate or $ZnCl_2$ for preparing formulation according to the invention, but this converts at a pH of 8 or 9 in an aqueous environment to ZnO, $Zn(OH)_2$ or ZnO.aq, which can be present in non-complexed or in complexed form.

Zinc salt may be present in those detergent compositions for cleaners according to the invention which are solid at room temperature are preferably present in the form of particles which have for example an average diameter (number-average) in the range from 10 nm to 100 μm, preferably 100 nm to 5 μm, determined for example by X-ray scattering.

Preferably, inventive solid detergent compositions for hard surface cleaning and inventive solid laundry detergent compositions comprise no measurable fractions of bismuth compounds, i.e. for example less than 1 ppm.

In one embodiment of the present invention, inventive solid detergent compositions for hard surface cleaning and inventive solid laundry detergent compositions comprise one or more further ingredient such as fragrances, dyestuffs, organic solvents, buffers, disintegrants for tabs, and/or acids such as methylsulfonic acid.

Preferred example detergent compositions for automatic dishwashing may be selected according to table 1.

TABLE 1

| Example detergent compositions for automatic dishwashing | | | |
|---|---|---|---|
| All amounts in g/sample | ADW.1 | ADW.2 | ADW.3 |
| inventive solid particles, rac MGDA-$Na_3$, (D50): 550 μm, mod II:I 20:1 | 30 | 22.5 | 15 |
| Protease | 2.5 | 2.5 | 2.5 |
| Amylase | 1 | 1 | 1 |
| n-$C_{18}H_{37}$—O($CH_2CH_2O)_9H$ | 5 | 5 | 5 |
| Polyacrylic acid $M_w$ 4000 g/mol as sodium salt, completely neutralized | 10 | 10 | 10 |
| Sodium percarbonate | 10.5 | 10.5 | 10.5 |
| TAED | 4 | 4 | 4 |
| $Na_2Si_2O_5$ | 2 | 2 | 2 |
| $Na_2CO_3$ | 19.5 | 19.5 | 19.5 |
| Sodium citrate dihydrate | 15 | 22.5 | 30 |
| HEDP | 0.5 | 0.5 | 0.5 |
| ethoxylated polyethylenimine, 20 EO/NH group, $M_n$: 30,000 g/mol | optionally: 0.1 | optionally: 0.1 | optionally: 0.1 |

Zinc salt may be present in those detergent compositions for home which are liquid at room temperature in dissolved or in solid or in colloidal form.

In one embodiment of the present invention, detergent compositions for cleaners and laundry detergent compositions comprise in total in the range from 0.05 to 0.4% by weight of zinc salt, based in each case on the solids content of the composition in question.

Here, the fraction of zinc salt is given as zinc or zinc ions. From this, it is possible to calculate the counterion fraction.

In one embodiment of the present invention, inventive solid detergent compositions for hard surface cleaning and inventive solid laundry detergent compositions are free from heavy metals apart from zinc compounds. Within the context of the present, this may be understood as meaning that detergent compositions for cleaners and laundry detergent compositions according to the invention are free from those heavy metal compounds which do not act as bleach catalysts, in particular of compounds of iron and of bismuth. Within the context of the present invention, "free from" in connection with heavy metal compounds is to be understood as meaning that the content of heavy metal compounds which do not act as bleach catalysts is in sum in the range from 0 to 100 ppm, determined by the leach method and based on the solids content. Preferably, formulation according to the invention has, apart from zinc, a heavy metal content below 0.05 ppm, based on the solids content of the formulation in question. The fraction of zinc is thus not included.

Within the context of the present invention, "heavy metals" are defined to be any metal with a specific density of at least 6 g/cm$^3$ with the exception of zinc. In particular, the heavy metals are metals such as bismuth, iron, copper, lead, tin, nickel, cadmium and chromium.

Laundry detergent compositions according to the invention are useful for laundering any type of laundry, and any type of fibres. Fibres can be of natural or synthetic origin, or they can be mixtures of natural of natural and synthetic fibres. Examples of fibers of natural origin are cotton and wool. Examples for fibers of synthetic origin are polyurethane fibers such as Spandex® or Lycra®, polyester fibers, or polyamide fibers. Fibers may be single fibers or parts of textiles such as knitwear, wovens, or nonwovens.

The invention is further illustrated by working examples.

WORKING EXAMPLES

General Remarks:

The X-ray powder diffractometer measurements were carried out on a D8 Advance® diffractometer from Bruker AXS (Karlsruhe). In reflection with Cu—K α-radiation was measured with a variable diaphragm adjustment on the primary side and on the secondary side. The measurement range was 2° to 80° 2-theta, the step width 0.010 and the measurement time per angle step 3.6 seconds. Based on the software TOPAS from Bruker optics, the relative amounts of the two polymorphic forms of (a) were determined.

Pore volumes were determined by nitrogen absorption

With exception of ee values and of degrees of crystallinity, percentages in the context of the examples refer to percent by weight unless expressly indicated otherwise.

Normal pressure: 1013 mbar. The abbreviation rpm stands for "rounds per minute".

Average particle diameters are (D50) values and are determined by sieving methods unless expressly noted otherwise.

Component (a.1): MGDA-$Na_3$ (ee: 11.4%, determined by HPLC with penicillamine as chiral modification agent), provided as 40% by weight aqueous solution, pH: 13.

Solid (b.1): ground alumina (92%), a packed bulk density of 769 kg/m$^3$, a total pore volume of 0.4 cm$^3$/g measure by N adsorption, and a specific surface area (BET) in the range of from 349 m$^2$/g. Impurities: only traces, less than 0.5% by weight, and about 8% by weight of moisture. Average particle diameter after grinding: 500 μm.

Solid (b2.): Si powder, a total pore volume of 0.5 cm$^3$/g

Step (A.1): in step (A.1); about one litre of a 40% by weight solution of component (a.1) was concentrated to 49% by weight by rotary evaporation at 75° C. and 250 mbar. 800 ml of the solution so provided was filled into a crystallizer with stirrer and baffles. The solution was maintained at 75° C. under stirring with 570 rpm.

Step (B.1): under stirring, 8.9 g (1% by weight) of (b.1) were added to the solution in the crystallizer.

Step (C.1): under continuous stirring, the solution was cooled down linearly to 45° C. within 4 hours. Crystal formation was observed. The resultant slurry was stirred at 45° C. for another 3 hours.

Step (D.1): The resultant slurry was then filtered. The pressure was raised to 0.5 bar and then to 1 bar. The resulting filter cake was dried at room temperature and under vacuum (ca. 200 mbar) for a period of 24 hours in a laboratory oven. Crystalline solid particles (SP.1) were obtained.

Step (E.1). some (SP.1) was milled down to an average particle diameter of 30 μm. Then, 12 g of (SP.1)—that contained (b.1)—were added to 1.2 kg of a 49% by weight solution of (a.1) at 75° C. Steps (C.1) and (D.1) were repeated accordingly. (SP.2) was obtained and analyzed.

The results are summarized in Table 2.

C-(SP.3): Solid MGDA-Na$_3$, spray granulated in accordance with EP 2 470 496 B1, example 1

TABLE 2

Powder XRD analysis of inventive solid particles and a comparison sample

| Sample   | Form I [%] | Form II [%] | Crystallinity [%] |
|----------|------------|-------------|-------------------|
| (SP.1)   | 5.7        | 94.3        | 87                |
| (SP.2)   | 6.7        | 93.3        | 86                |
| C-(SP.3) | 96         | 4           | 74                |

Moisture uptake and percarbonate stability tests

Samples of (SP.1), (SP.2) and C-(SP.3) were each stored for 7 days at 35° C. and a relative humidity of 70%. The weight increase corresponds to the moisture uptake.

In order to measure the percarbonate stability, the samples were stored for 26 days at 35° C. and a relative humidity of 70%. The samples were stored in 50 ml glass vials having a lid with a 0.5 mm hole. The change in color was followed my measuring elrepho brightness values. The higher the elrepho brightness value the darker the sample.

The results are summarized in Table 3.

TABLE 3

Properties of inventive solid particles and a comparison sample

| Sample   | Moisture uptake [%] | Colour after 15 days | Colour after 25 days |
|----------|---------------------|----------------------|----------------------|
| (SP.1)   | 4.8                 | 5.96                 | 6.43                 |
| (SP.2)   | 5.2                 | 6.82                 | 7.6                  |
| C-(SP.3) | 19.7                | 22.3                 | 36.7                 |

The invention claimed is:

1. Solid particles of methylglycine diacetate (MGDA) alkali metal salt (a), comprising
   (a1) from 1 to 10% by weight of a monoclinic alkali metal salt of MGDA, and
   (a2) from 90 to 99% by weight of an orthorhombic alkali metal salt of MGDA, based on a total content of (a1) and (a2).

2. The solid particles of claim 1, wherein (a) is selected from compounds according to general formula (I)

[CH$_3$—CH(COO)—N(CH$_2$—COO)$_2$]M$_{3-x}$H$_x$    (I)

wherein

M is selected from alkali metal cations, same or different, and x is in a range of from 0 to 1.0.

3. The solid particles of claim 1, wherein said alkali metal salt of (a) is a trisodium salt.

4. The solid particles of claim 1, wherein from 0.1 to 30% of the solid particles comprise a residual particulate solid (b).

5. The solid particles of claim 1, further comprising a particulate solid (b), wherein said particulate solid (b) is selected from the group consisting of ground molecular sieves, ground alumina and silicon.

6. The solid particles of claim 1, further comprising a particulate solid (b), wherein said particulate solid (b) is alumina.

7. A process for making a cleaning agent comprising a peroxide or a percarbonate, the process comprising adding the solid particles of claim 1 to a composition, to obtain the cleaning agent.

8. A process for making the solid methylglycine diacetate (MGDA) alkali metal salt (a) according to claim 1, said process comprising:
   (A) providing an aqueous solution comprising 35 to 60% by weight of said MGDA alkali metal salt and having a temperature in a range of from 50 to 90° C.,
   (B) adding 0.01 to 2% by weight, based on a content of (a), of a particulate solid (b) with a pore volume in a range of from 0.25 to 0.75 cm$^3$/g, determined by nitrogen adsorption in accordance with 66134:1998-02,
   (C) crystallizing (a), to obtain a crystalline (a) and
   (D) removing said crystalline (a) from the mother liquor.

9. The process of claim 8, wherein said particulate solid (b) is selected from the group consisting of ground molecular sieves, ground alumina and ground silicon.

10. The process of claim 8, wherein (b) has an average particle diameter in a range of from 350 to 750 μm, determined by sieving.

11. The process of claim 8, wherein (a) is selected from compounds according to general formula (I)

[CH$_3$—CH(COO)—N(CH$_2$—COO)$_2$]M$_{3-x}$H$_x$    (I)

wherein

M is selected from alkali metal cations, same or different, and x is in a range of from 0 to 1.0.

12. The process of claim 8, wherein (C) comprises decreasing the temperature by 20 to 80° C.

13. The process of claim 8, wherein said particulate solid (b) is alumina.

14. The process of claim 8, wherein said solid MGDA alkali metal salt (a) has a residual moisture content in a range of from 0.5 to 20% by weight.

15. The process of claim 8, further comprising:
(E) adding the mother liquor from (D), in whole or in part, to an aqueous solution of MGDA alkali metal salt (a) and adjusting a concentration of the aqueous solution to 35 to 60% by weight of MGDA alkali metal salt (a).

* * * * *